US009554097B2

(12) United States Patent
Sasaki et al.

(10) Patent No.: US 9,554,097 B2
(45) Date of Patent: Jan. 24, 2017

(54) ENDOSCOPE IMAGE PROCESSING DEVICE, ENDOSCOPE SYSTEM, AND IMAGE PROCESSING METHOD

(71) Applicants: OLYMPUS CORPORATION, Shibuya-ku, Tokyo (JP); OLYMPUS MEDICAL SYSTEMS CORP., Shibuya-ku, Tokyo (JP)

(72) Inventors: Hiroshi Sasaki, Hachioji (JP); Kazuki Honda, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 305 days.

(21) Appl. No.: 14/225,085

(22) Filed: Mar. 25, 2014

(65) Prior Publication Data

US 2014/0204187 A1 Jul. 24, 2014

Related U.S. Application Data

(63) Continuation of application No. PCT/JP2012/073401, filed on Sep. 13, 2012.

(30) Foreign Application Priority Data

Sep. 26, 2011 (JP) ................................. 2011-208734

(51) Int. Cl.
*A62B 1/04* (2006.01)
*H04N 7/18* (2006.01)
(Continued)

(52) U.S. Cl.
CPC ............. *H04N 7/18* (2013.01); *A61B 1/00009* (2013.01); *A61B 1/00174* (2013.01);
(Continued)

(58) Field of Classification Search
CPC .................................................. G02B 23/2415
(Continued)

(56) References Cited

U.S. PATENT DOCUMENTS 6,466,701 B1 * 10/2002 Ejiri ...................... G06T 7/0024
348/135
8,419,630 B2 4/2013 Kase et al.
(Continued)

FOREIGN PATENT DOCUMENTS

JP 09-313435 A 12/1997
JP 09313435 A * 12/1997
(Continued)

OTHER PUBLICATIONS

International Search Report (ISR) dated Nov. 20, 2012 (and English translation thereof) issued in International Application No. PCT/JP2012/073401.
(Continued)

*Primary Examiner* — Hung Dang
*Assistant Examiner* — Girumsew Wendmagegn
(74) *Attorney, Agent, or Firm* — Holtz, Holtz & Volek PC

(57) ABSTRACT

An endoscope image processing device includes an image acquisition section and a boundary region correction section. The image acquisition section acquires image signals that form a front image corresponding to a front field of view and a side image corresponding to a side field of view as a single acquired image. A region within the acquired image that corresponds to the front field of view is referred to as a front region, and a region within the acquired image that corresponds to the side field of view is referred to as a side region. The boundary area correction section performs a process that causes at least one of an image of the front region and
(Continued)

an image of the side region to overlap a boundary region that is a region that defines a boundary between the front region and the side region.

17 Claims, 12 Drawing Sheets

(51) Int. Cl.
 *A61B 1/00* (2006.01)
 *G06T 3/00* (2006.01)
 *G06T 7/00* (2006.01)

(52) U.S. Cl.
 CPC .......... *G06T 3/0062* (2013.01); *G06T 7/0028* (2013.01); *G06T 2207/10024* (2013.01); *G06T 2207/10068* (2013.01); *G06T 2207/20221* (2013.01)

(58) Field of Classification Search
 USPC ..................................................... 348/45, 65
 See application file for complete search history.

(56) References Cited

U.S. PATENT DOCUMENTS

| | | |
|---|---|---|
| 2005/0033117 A1 | 2/2005 | Ozaki et al. |
| 2008/0118155 A1 | 5/2008 | Yamashita |
| 2010/0171810 A1 | 7/2010 | Ohki |
| 2010/0195007 A1 | 8/2010 | Takahashi |
| 2011/0275889 A1* | 11/2011 | Kase .................. A61B 1/00009 600/103 |

FOREIGN PATENT DOCUMENTS

| | | |
|---|---|---|
| JP | 2005211532 A | 8/2005 |
| JP | 2010-117665 A | 5/2010 |
| JP | 2010-169792 A | 8/2010 |
| JP | 2011-152202 A | 8/2011 |
| WO | WO 2011/055614 A1 | 5/2011 |

OTHER PUBLICATIONS

Extended European Search Report dated Feb. 4, 2015, issued in counterpart European Application No. 12836098.9.

* cited by examiner

FIG. 11

| R | G | R | G |
|---|---|---|---|
| G | B | G | B |
| R | G | R | G |
| G | B | G | B |

ENDOSCOPE IMAGE PROCESSING DEVICE, ENDOSCOPE SYSTEM, AND IMAGE PROCESSING METHOD

CROSS REFERENCE TO RELATED APPLICATION

This application is a continuation of International Patent Application No. PCT/JP2012/073401, having an international filing date of Sep. 13, 2012, which designated the United States, the entirety of which is incorporated herein by reference. Japanese Patent Application No. 2011-208734 filed on Sep. 26, 2011 is also incorporated herein by reference in its entirety.

BACKGROUND

The present invention relates to an endoscope image processing device, an endoscope system, an image processing method, and the like.

It has been desired to improve the lesion detection accuracy within a body cavity during endoscopic diagnosis, and an endoscopic scope including a wide-angle optical system having an angle of view of 170° has been developed.

When using such an endoscopic scope, an area situated on the back side of the side field view (e.g., the back of large folds of an internal organ such as a large intestine) may not lie within the field-of-view range, and it may be difficult to acquire an image of a lesion present in such an area.

For example, an endoscopic scope that includes a fish-eye lens having an angle of view equal to or more than 180° may be used to observe an area situated on the back side of the side field view (e.g., the back of folds).

JP-A-2010-117665 discloses an optical system allows enables simultaneous observation of the front field of view and the side field of view. The optical system disclosed in JP-A-2010-117665 is effective for observing the back of the folds of the large intestine or the like since distortion in the peripheral region of the image that corresponds to the side field of view can be reduced.

SUMMARY

According to one aspect of the invention, there is provided an endoscope image processing device comprising:

an image acquisition section that acquires image signals that form a front image corresponding to a front field of view and a side image corresponding to a side field of view as a single acquired image; and a boundary region correction section that performs an overlapping process that causes at least one of an image of a front region and an image of a side region to overlap a boundary region that is a region that defines a boundary between the front region and the side region, the front region being a region within the acquired image that corresponds to the front field of view, and the side region being a region within the acquired image that corresponds to the side field of view, the boundary region being a region that corresponds to a specific angle of view based on an optical design value of an optical system for capturing the front field of view and the side field of view, a first boundary line that is a boundary line between the boundary region and the front region being set on an inner side relative to the region that corresponds to the specific angle of view, and a second boundary line that is a boundary line between the boundary region and the side region being set on an outer side relative to the region that corresponds to the specific angle of view.

According to another aspect of the invention, there is provided an endoscope system comprising:

the above endoscope image processing device;

a front observation optical system for capturing the front field of view;

a side observation optical system for capturing the side field of view; and an image sensor that simultaneously captures the front field of view and the side field of view.

According to another aspect of the invention, there is provided an image processing method comprising:

acquiring image signals that form a front image corresponding to a front field of view and a side image corresponding to a side field of view as a single acquired image;

setting a region that corresponds to a specific angle of view based on an optical design value of an optical system for capturing the front field of view and the side field of view to be a boundary region, setting a first boundary line that is a boundary line between the boundary region and a front region on an inner side relative to the region that corresponds to the specific angle of view, and setting a second boundary line that is a boundary line between the boundary region and a side region on an outer side relative to the region that corresponds to the specific angle of view, the boundary region being a region that defines a boundary between the front region and the side region, the front region being a region within the acquired image that corresponds to the front field of view, and the side region being a region within the acquired image that corresponds to the side field of view; and performing an overlapping process that causes at least one of an image of the front region and an image of the side region to overlap the boundary region.

BRIEF DESCRIPTION OF THE DRAWINGS

FIG. 11 is a schematic view illustrating a Bayer pixel array.

DESCRIPTION OF EXEMPLARY EMBODIMENTS

Several embodiments of the invention may provide an endoscope image processing device, an endoscope system, an image processing method, and the like that can suppress a deterioration in visibility due to the boundary region.

According to one embodiments of the invention, there is provided an endoscope image processing device comprising:

an image acquisition section that acquires image signals that form a front image corresponding to a front field of view and a side image corresponding to a side field of view as a single acquired image; and a boundary region correction section that performs an overlapping process that causes at least one of an image of a front region and an image of a side region to overlap a boundary region that is a region that defines a boundary between the front region and the side region, the front region being a region within the acquired image that corresponds to the front field of view, and the side region being a region within the acquired image that corresponds to the side field of view.

According to one embodiments of the invention, the image signals that form the front image and the side image as a single acquired image are acquired, and the process that causes at least one of the image of the front region and the image of the side region to overlap the boundary region is performed. The above configuration makes it possible to suppress a deterioration in visibility due to the boundary region.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Outline

Figure 4B:
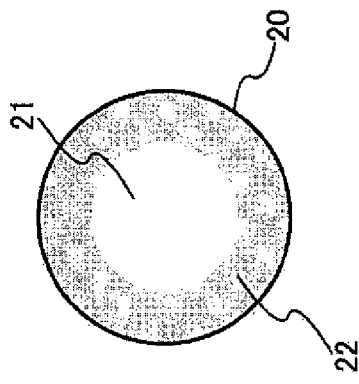
FIGS. 4A and 4B illustrate a detailed configuration example of an objective lens.
Figure 4C:
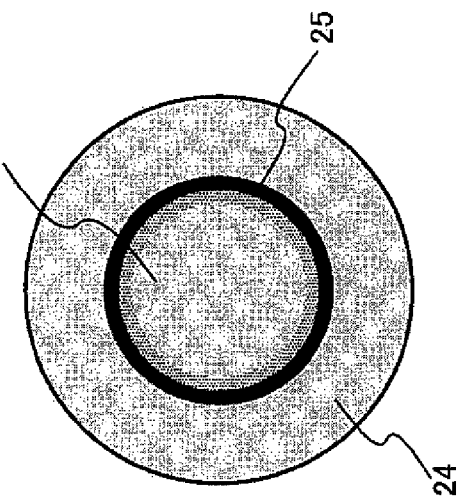
FIG. 4C is a view illustrating an image captured through the objective lens.
Figure 4A:
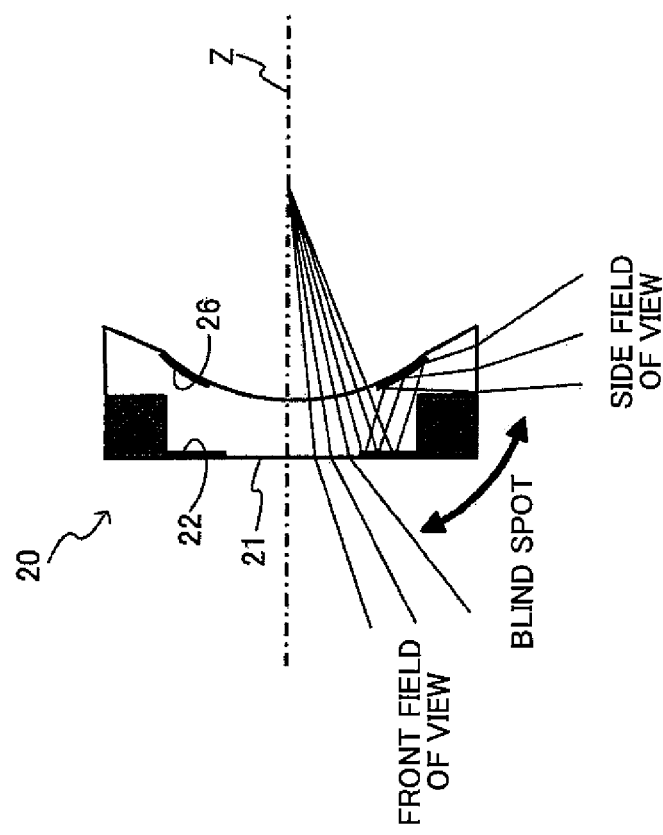

An optical system included in an endoscope system according to several embodiments of the invention includes a catoptric system for observing the side field of view, and a dioptric system for observing the front field of view (see FIG. 4A and the like). When an image is captured using the above optical system, shading occurs in the boundary region between the field of view of the catoptric system and the field of view of the dioptric system. When the large intestine is observed in a state in which shading locally occurs, shading in the boundary region may be erroneously determined to be a shadow of folds even if no folds are present in the boundary region.

According to several embodiments of the invention, a region FR that corresponds to the front field of view or a region SR that corresponds to the side field of view is magnified, and the magnified region is caused to overlap the boundary region between the front field of view and the side field of view (see FIG. 6A to 7E and the like). According to the above configuration, since shading that occurs due to the optical system can be eliminated from the display image, it is possible to prevent a situation in which the boundary region is erroneously determined to be a shadow of the folds of the large intestine. Therefore, it is possible to implement a wide-field endoscope system that achieves high visibility.

2. First Embodiment

2.1. Endoscope System

Figure 1:
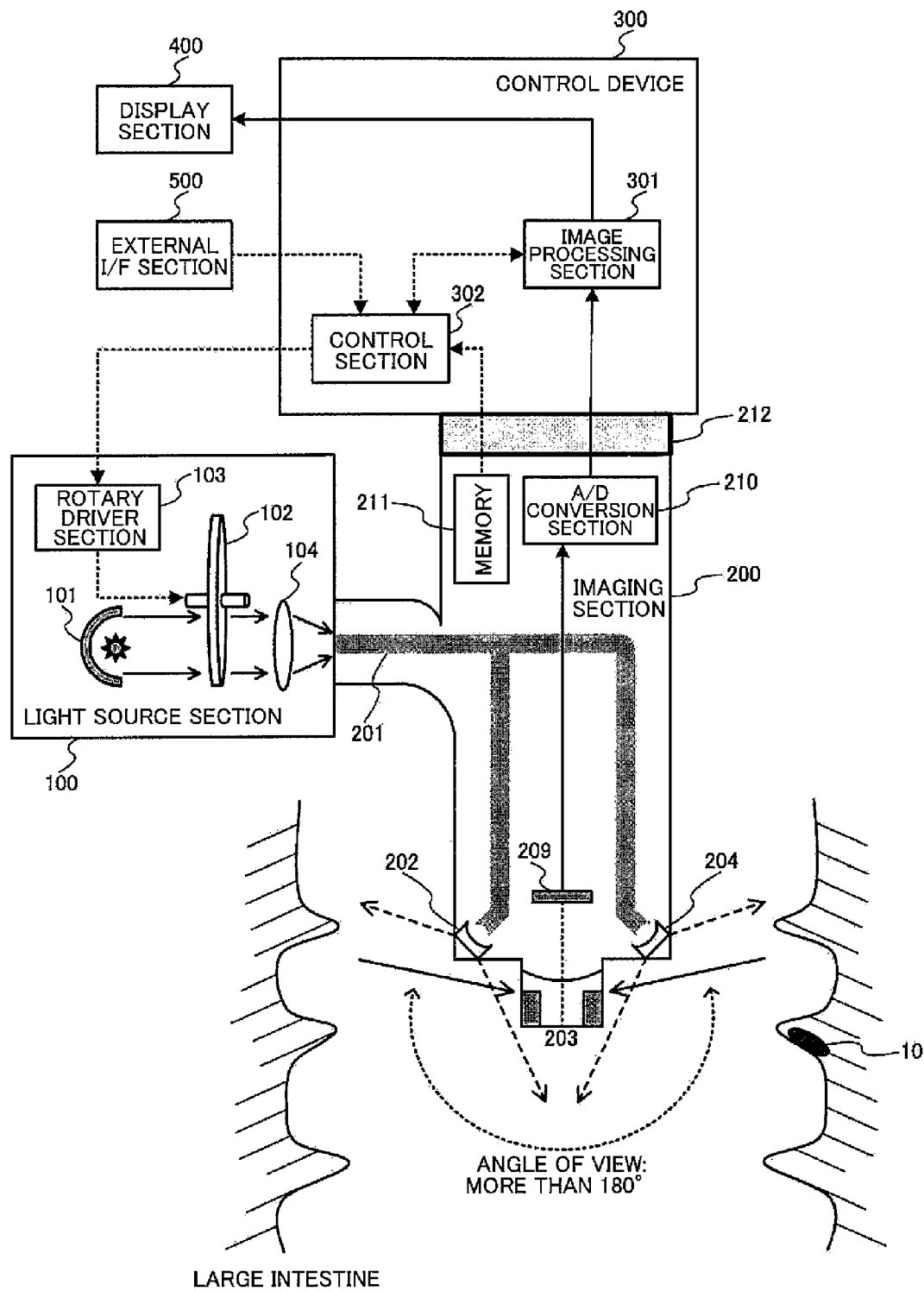
FIG. 1 illustrates a first configuration example of an endoscope system.

FIG. 1 illustrates a first configuration example of an endoscope system. The endoscope system includes a light source section 100, an imaging section 200, a control device 300 (processor section), a display section 400, and an external OF section 500.

The light source section 100 includes a white light source 101, a rotary color filter 102 that has a plurality of spectral transmittances, a rotary driver section 103 that drives the rotary color filter 102, and a condenser lens 104 that focuses the light that has passed through the rotary color filter 102 and has spectral characteristics on the incident end face of a light guide fiber 201.

Figure 2:
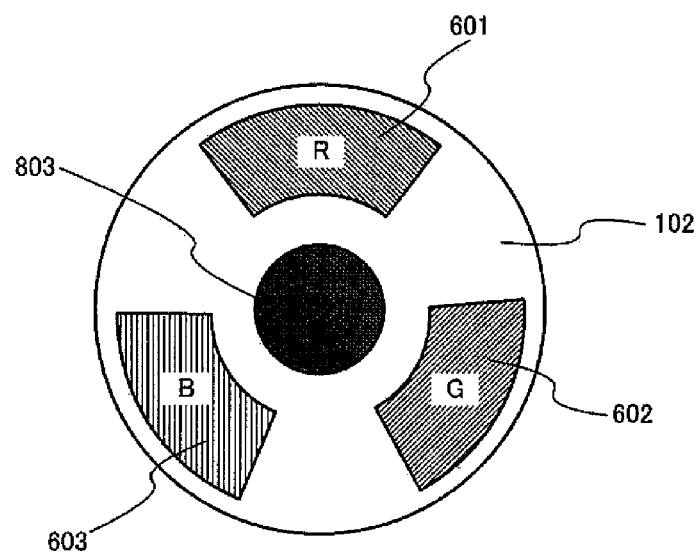
FIG. 2 illustrates a detailed configuration example of a rotary color filter.
Figure 3:
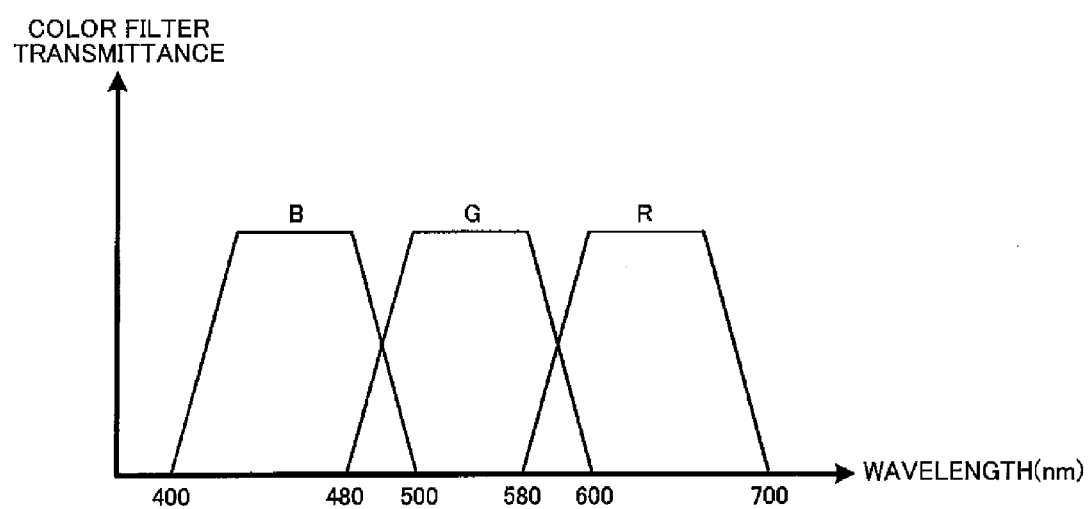
FIG. 3 illustrates an example of the spectral transmittance characteristics of a color filter.

As illustrated in FIG. 2, the rotary color filter 102 includes a red (R) color filter 601, a green (G) color filter 602, a blue (B) color filter 603, and a rotary motor 803, for example. FIG. 3 illustrates the spectral characteristics of these color filters.

The rotary driver section 103 rotates the rotary color filter 102 at a given rotational speed in synchronization with the imaging period of an image sensor 209 based on a control signal output from a control section 302 included in the control device 300. For example, when the rotary color filter 102 is rotated at 20 revolutions per second, each color filter crosses the incident white light every 1/60th of a second. In this case, the image sensor 209 captures reflected light from the observation target to which each color light (R, G, or B) is applied, and transfers the resulting image every 1/60th of a second. Specifically, the endoscope system according to the first embodiment frame-sequentially captures an R image, a G image, and a B image every 1/60th of a second (i.e., the frame rate is 20 frames per second (fps)).

The imaging section 200 is formed to be elongated and flexible (i.e., can be curved) so that the imaging section 200 can be inserted into a body cavity (e.g., large intestine), for example. The imaging section 200 includes the light guide fiber 201 that guides the light focused by the light source section 100, and illumination lenses 202 and 204 that diffuse the light guided by the light guide fiber 201, and apply the diffused light to the observation target. The imaging section 200 also includes an objective lens 203 that focuses reflected light from the observation target, the image sensor 209 that detects the focused light, and an A/D conversion section 210 that converts photoelectrically converted analog signals output from the image sensor 209 into digital signals. The imaging section 200 further includes a memory 211, and a connector 212 for removably connecting the imaging section 200 to the control device 300.

The memory 211 stores extraction boundary information about the front-field-of-view image and the side-field-of-view image, display magnification information about the front-field-of-view image and the side-field-of-view image, and specific information relating to a production variation specific to the imaging section 200 (described later).

The image sensor 209 is a single-chip monochrome image sensor. For example, a CCD image sensor, a CMOS image sensor, or the like may be used as the image sensor 209.

The objective lens 203 includes an optical system that achieves an angle of view equal to or more than 180° by combining a front observation optical system and a side observation optical system (described later), and enables observation of a lesion area 10 situated on the back of the folds of the large intestine, for example.

The illumination lenses 202 and 204 are disposed to face outward with respect to the optical axis of the objective lens 203 so that the observation target within the angle of view of the objective lens 203 can be uniformly illuminated. In the first embodiment, the light guide fiber 201 that consists of several thousand elements is divided into two parts. Note that the light guide fiber 201 may be divided into three or more parts, and illumination lenses corresponding to the respective parts may be disposed on the end of the endoscopic scope. This makes it possible to more uniformly illuminate a wide-viewing-angle area. A number of light-emitting devices (e.g., LED or organic EL devices) may be disposed on the end of the endoscopic scope.

The control device 300 includes an image processing section 301 that corrects a boundary region between the front-field-of-view image and the side-field-of-view image, and a control section 302 that controls each section of the endoscope system.

The display section 400 is implemented by a display device (e.g., CRT or liquid crystal monitor) that can display a movie.

The external I/F section 500 serves as an interface that allows the user to perform an input operation and the like on the endoscope system. For example, the external I/F section 500 includes a power switch (power ON/OFF switch), a shutter button (imaging operation start button), a mode (e.g., imaging mode) switch (e.g., a switch for manually changing the display area ratio of the front-field-of-view image to the side-field-of-view image), and the like. The external I/F section 500 outputs the input information to the control section 302.

2.2. Objective Lens

FIG. 4A illustrates a detailed configuration example of the objective lens for observing the front field of view and the side field of view. As illustrated in FIG. 4A, light from the front field of view is incident on the front surface of a lens 20, and light from the side field of view is incident on the side surface of the lens 20. Light incident from the front field of view passes through a transmission part 21 (refractive part) of the lens 20, and is guided to the image sensor 209. Light incident from the side field of view is reflected by the reflective parts 26 and 22 of the lens 20, and is guided to the imaging section 200.

When the lens 20 is observed from the front side along the optical axis Z (see FIG. 4B), the lens 20 consists of the transmission part 21 (transmission area) that allows light incident from the front field of view to pass through, and the reflective part 22 (reflective area) that reflects light incident from the side field of view. When using such an optical system, part of reflected light from the object within the front field of view is blocked in the boundary region between the reflective part 22 and the transmission part 21. As a result, shading occurs in the boundary region between a front-field-of-view image 23 and a side-field-of-view image 24 formed on the image sensor (see FIG. 4C). A black zonal annular region 25 is formed in the boundary region due to shading.

Note that the term "front field of view" used herein refers to a front field-of-view range that includes the optical axis direction. For example, the front field of view refers to a range of 0 to 70° with respect to the optical axis. The term "side field of view" used herein refers to a side field-of-view range that includes a direction orthogonal to the optical axis.

For example, the side field of view refers to a range of 70 to 135° with respect to the optical axis. The objective lens 203 according to the first embodiment has a field-of-view range of 0 to 110° with respect to the optical axis, for example.

The term "shading" used herein refers to a shadow (shade) in an image (i.e., a region of an image that is darker than other regions (e.g., has a brightness lower than that of other regions) due to the optical system). For example, a blind spot due to the lens 20 occurs between the front field of view and the side field of view (see FIG. 4A), and a shadow in the image that corresponds to the blind spot is referred to as "shading". Light incident from the front field of view that passes through the transmission part 21 may show limb darkening (i.e., shading) due to mechanical vignetting that occurs due to the optical system, for example.

2.3. Image Processing Section

Figure 5:
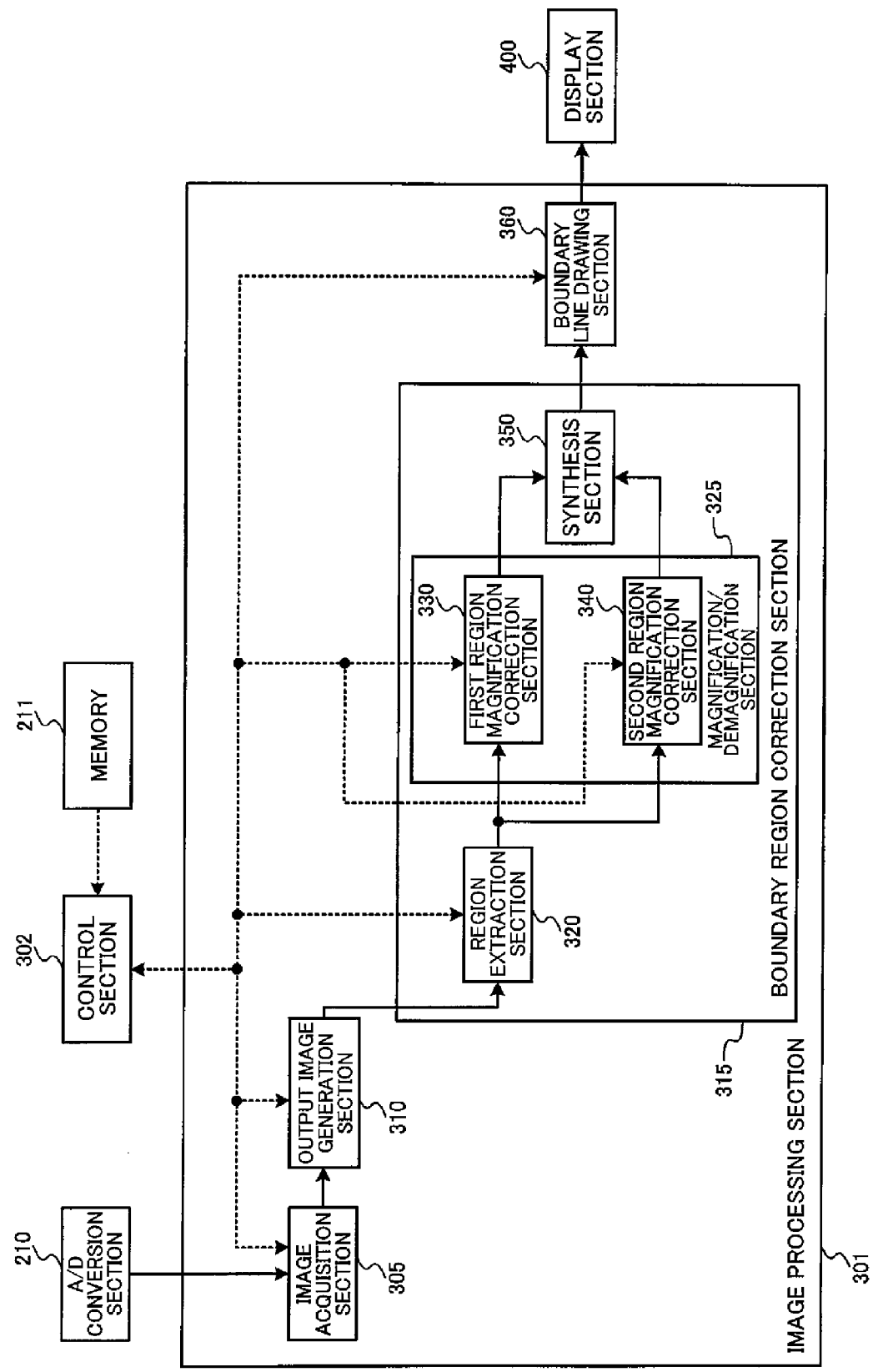
FIG. 5 illustrates a first detailed configuration example of an image processing section.

FIG. 5 illustrates a first detailed configuration example of the image processing section 301. The image processing section 301 includes an image acquisition section 305, an output image generation section 310, a boundary region correction section 315, and a boundary line drawing section 360. The boundary region correction section 315 includes a region extraction section 320, a magnification/demagnification section 325, and a synthesis section 350. The magnification/demagnification section 325 includes a first region magnification correction section 330 and a second region magnification correction section 340.

The connection relationship and the flow of data between each section are described below. The captured image output from the A/D conversion section 210 is input to the image acquisition section 305. The control section 302 is connected to the image acquisition section 305, the output image generation section 310, the region extraction section 320, the first region magnification correction section 330, the second region magnification correction section 340, and the boundary line drawing section 360. The information specific to the imaging section 200 (e.g., the extraction boundary information about the front-field-of-view image and the side-field-of-view image, and the display magnification information about the front-field-of-view image and the side-field-of-view image) that is stored in the memory 211 is input to the control section 302.

The image acquisition section 305 acquires a single image obtained by capturing the front field of view and the side field of view, and outputs the acquired image to the output image generation section 310. Specifically, the front field of view and the side field of view are simultaneously captured as a single image using the lens 20, and the image acquisition section 305 acquires the single image. Note that the front field of view and the side field of view need not necessarily be simultaneously captured. For example, the front field of view and the side field of view may be sequentially captured by a different imaging operation, and the image acquisition section 305 may synthesize the front-field-of-view image and the side-field-of-view image to acquire a single image.

The output image generation section 310 converts the input captured image into an image format that can be displayed on a display monitor based on an output image generation parameter (e.g., OB clamp, white balance, γ conversion table, enhancement coefficient, and magnification) output from the control section 302, and outputs the resulting image to the region extraction section 320 as an output image.

The boundary region correction section 315 performs a correction process that causes at least one of the front-field-of-view image and the side-field-of-view image to overlap the boundary region between the front-field-of-view image and the side-field-of-view image to reduce the boundary region. The extraction boundary information about the front-field-of-view image and the side-field-of-view image stored in the memory 211 is input to the region extraction section 320 through the control section 302. The front-field-of-view image extracted by the region extraction section 320 from the output image is output to the first region magnification correction section 330. The side-field-of-view image extracted by the region extraction section 320 from the output image is output to the second region magnification correction section 340.

The first region magnification correction section 330 performs a magnification/demagnification process on the input front-field-of-view image based on magnification information output from the control section 302, and outputs the front-field-of-view image subjected to the magnification/demagnification process to the synthesis section 350. A magnification process, a unit magnification process (that does not change the magnification), or a demagnification process based on the magnification information is appropriately performed on the front-field-of-view image as the magnification/demagnification process. The magnification/demagnification process is preferably performed along the radial direction (diametrical direction) relative to the center of the front-field-of-view image.

The second region magnification correction section 340 performs a magnification/demagnification process on the input side-field-of-view image based on the magnification information output from the control section 302, and outputs the side-field-of-view image subjected to the magnification/demagnification process to the synthesis section 350. A magnification process, a unit magnification process (that does not change the magnification), or a demagnification process based on the magnification information is appropriately performed on the side-field-of-view image as the magnification/demagnification process.

The synthesis section 350 causes the front-field-of-view image subjected to the magnification/demagnification process that is output from the first region magnification correction section 330 and the side-field-of-view image subjected to the magnification/demagnification process that is output from the second region magnification correction section 340 to overlap each other in the boundary region to generate a synthesized image, and outputs the synthesized image to the boundary line drawing section 360. The front-field-of-view image subjected to the magnification/demagnification process may be caused to overlap the side-field-of-view image subjected to the magnification/demagnification process, or the side-field-of-view image subjected to the magnification/demagnification process may be caused to overlap the front-field-of-view image subjected to the magnification/demagnification process. The front-field-of-view image subjected to the magnification/demagnification process may be caused to overlap the side-field-of-view image subjected to the magnification/demagnification process in an area of the boundary region situated on the side of the front-field-of-view image, and the side-field-of-view image subjected to the magnification/demagnification process may be caused to overlap the front-field-of-view image subjected to the magnification/demagnification process in an area of the boundary region situated on the side of the side-field-of-view image.

The boundary line drawing section 360 draws a boundary line in a given color within the synthesized image output from the synthesis section 350 based on overlap boundary position information about the front-field-of-view image and the side-field-of-view image output from the control section 302, and outputs the resulting image to the display section 400. The given color may be a fixed color (e.g., black), or may be a color opposite the color in the peripheral region, for example. It suffices that the boundary line that is drawn by the boundary line drawing section 360 define the boundary between the front-field-of-view image and the side-field-of-view image that have been synthesized. The boundary line may be a solid line, a broken line, or the like, for example.

A process that corrects the boundary region between the front-field-of-view image and the side-field-of-view image using the front-field-of-view image is described below with reference to FIGS. 6A to 6E (schematic views).

Figure 6A:
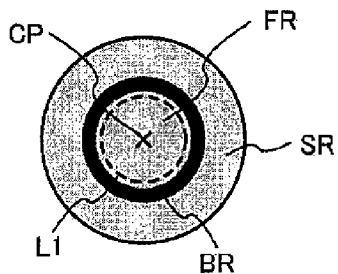
FIGS. 6A to 6E are views illustrating a process that corrects a boundary region.

FIG. 6A illustrates the output image output from the output image generation section 310. The output image includes a front-field-of-view image FR, a side-field-of-view image SR, and a boundary region BR. L1 is an extraction boundary line for extracting the front-field-of-view image FR. CP is the center position of the front-field-of-view image FR.

Figure 6B:
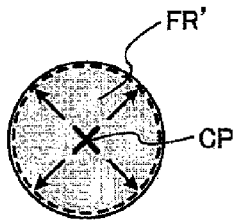

As illustrated in FIG. 6B, the region extraction section 320 extracts the front-field-of-view image FR based on the extraction boundary line L1 output from the control section 302. The first region magnification correction section 330 magnifies the extracted front-field-of-view image FR in the radial direction around the center position CP output from the control section 302 based on the magnification information output from the control section 302.

Figure 6C:
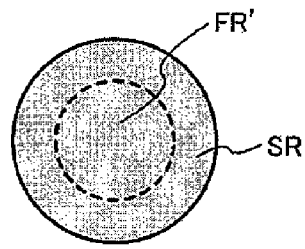

As illustrated in FIG. 6C, the synthesis section 350 causes the magnified front-field-of-view image FR' output from the first region magnification correction section 330 to overlap the side-field-of-view image SR (that is not magnified or demagnified) output from the second region magnification correction section 340. The image thus synthesized is output as a synthesized image.

Figure 6D:
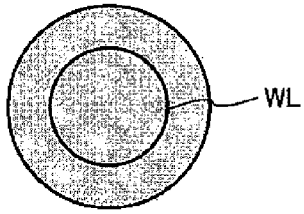

As illustrated in FIG. 6D, the boundary line drawing section 360 draws a boundary line WL along the overlap boundary of the synthesized image output from the synthesis section 350. The resulting image is output as a synthesized image in which the front-field-of-view image and the side-field-of-view image are clearly defined by the boundary line. The overlap boundary is the outer edge of the front-field-of-view image FR' that overlaps the side-field-of-view image SR, for example.

Figure 6E:
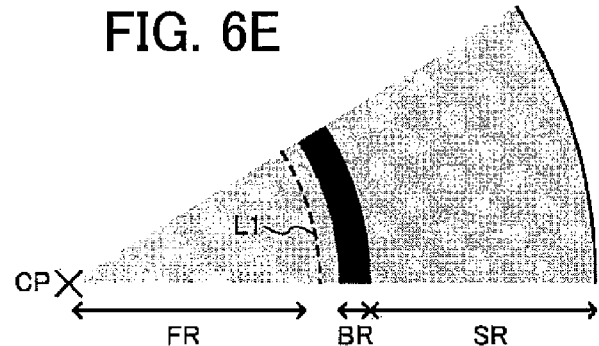

As illustrated in FIG. 6E, the front-field-of-view image FR (i.e., the image of the front region) is the image extracted along the extraction boundary line L1 (first boundary line), and the side-field-of-view image SR is the image captured through the side observation optical system (i.e., the reflective parts 22 and 26 in FIG. 4A). The boundary region BR is a shading region that occurs due to the blind spot of the optical system and/or limb darkening.

A process that corrects the boundary region between the front-field-of-view image and the side-field-of-view image using the side-field-of-view image is described below with reference to FIGS. 7A to 7E (schematic views).

Figure 7A:
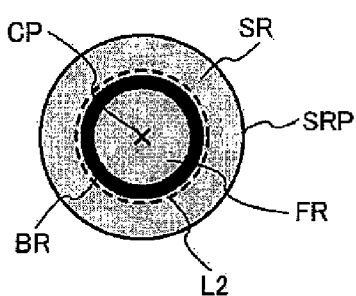
FIGS. 7A to 7E are views illustrating a process that corrects a boundary region.

In FIG. 7A, L2 is an extraction boundary line for extracting the side-field-of-view image SR. SRP is the outer edge of the side-field-of-view image SR.

Figure 7B:
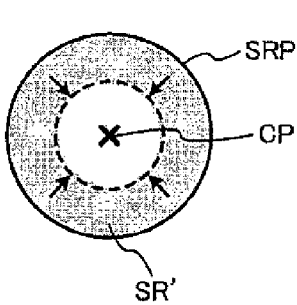

As illustrated in FIG. 7B, the region extraction section 320 extracts the side-field-of-view image SR based on the extraction boundary line L2 output from the control section 302. The second region magnification correction section 340 magnifies the extracted side-field-of-view image SR in the radial direction toward the center position CP relative to the outer edge SRP output from the control section 302 based on the magnification information output from the control section 302.

Figure 7C:
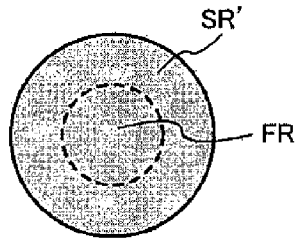

As illustrated in FIG. 7C, the synthesis section 350 causes the magnified side-field-of-view image SR' output from the second region magnification correction section 340 to overlap the front-field-of-view image FR (that is not magnified or demagnified) output from the first region magnification correction section 330. The image thus synthesized is output as a synthesized image.

Figure 7D:
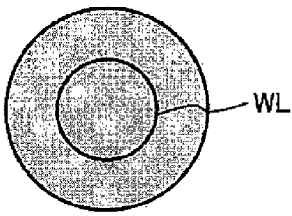

As illustrated in FIG. 7D, the boundary line drawing section 360 draws the boundary line WL along the overlap boundary of the synthesized image output from the synthesis section 350. The resulting image is output as a synthesized image in which the front-field-of-view image and the side-field-of-view image are clearly defined by the boundary line. The overlap boundary is the inner edge of the side-field-of-view image SR' that overlaps the front-field-of-view image FR, for example.

Figure 7E:
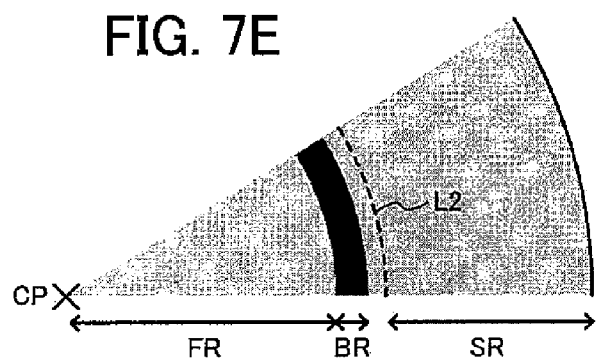

As illustrated in FIG. 7E, the front-field-of-view image FR is the image captured through the front observation optical system (i.e., the transmission part 21 in FIG. 4A), and the side-field-of-view image SR (i.e., the image of the side region) is the image extracted along the extraction boundary line L2 (second boundary line).

The extraction boundary line L1 for extracting the front-field-of-view image and the extraction boundary line L2 for extracting the side-field-of-view image are set by capturing a uniform color chart (e.g., gray patch), for example. Specifically, a first circle that belongs to the front-field-of-view image and a second circle that belongs to the side-field-of-view image are set within an image that includes the chart. The first circle and the second circle are concentric circles (i.e., circles having a common center point). The first circle and the second circle that differ in radius to a minimum extent in a state in which the absolute value of the difference in pixel value between two pixels that respectively correspond to the nearest points on the circumference of the first circle and the circumference of the second circle is within a given value, are set to be the extraction boundary line L1 and the extraction boundary line L2. According to the above method, since the difference in pixel value can be made smaller than a given value at the overlap boundary, a natural image can be displayed.

Although an example in which one of the front-field-of-view image and the side-field-of-view image is subjected to the magnification/demagnification process has been described above, both the front-field-of-view image and the side-field-of-view image may be subjected to the magnification/demagnification process, and synthesized to correct the boundary region.

The magnification/demagnification process performed by the magnification/demagnification section 325 is described below with reference to FIGS. 8A to 8C.

Figure 8A:
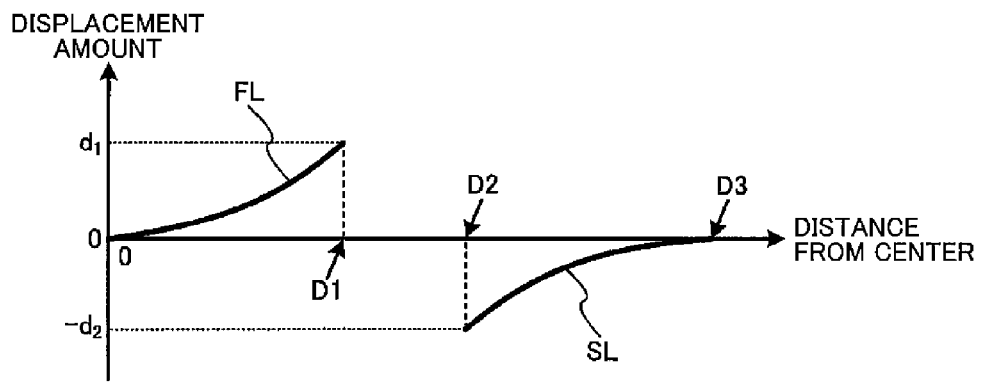
FIGS. 8A to 8C are views illustrating a magnification/demagnification process.

As illustrated in FIG. 8A, when both the front-field-of-view image and the side-field-of-view image are magnified to correct the boundary region, the displacement amount due to the magnification/demagnification process is positive in the front-field-of-view image, and is negative in the side-field-of-view image.

In FIG. 8A, the horizontal axis of the graph indicates the distance from the center of the front-field-of-view image and the side-field-of-view image (the center of the front-field-of-view image and the side-field-of-view image have a common center position), and the vertical axis of the graph indicates the cumulative displacement amount. The start point of the cumulative displacement amount of the front-field-of-view image is the center of the front-field-of-view image, and the start point of the cumulative displacement amount of the side-field-of-view image is the outer edge of the side-field-of-view image. FL indicates the characteristic line of the displacement amount of the front-field-of-view image, and SL indicates the characteristic line of the displacement amount of the side-field-of-view image. D1 indicates the distance from the center of the front-field-of-view image to the extraction boundary line, D2 indicates the distance from the center of the side-field-of-view image to the extraction boundary line, and D3 indicates the distance from the center to the outer edge of the side-field-of-view image.

Figure 8B:
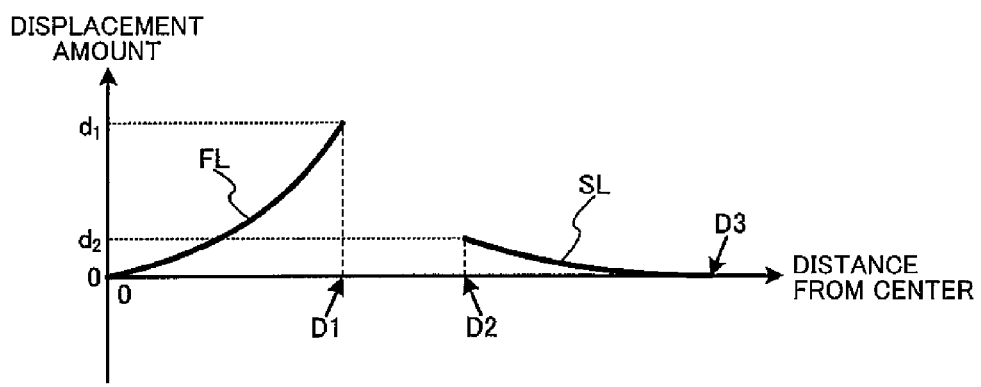

As illustrated in FIG. 8B, when the front-field-of-view image is magnified, and the side-field-of-view image is demagnified to correct the boundary region, the displacement amount due to the magnification/demagnification process is positive in the front-field-of-view image and the side-field-of-view image.

Figure 8C:
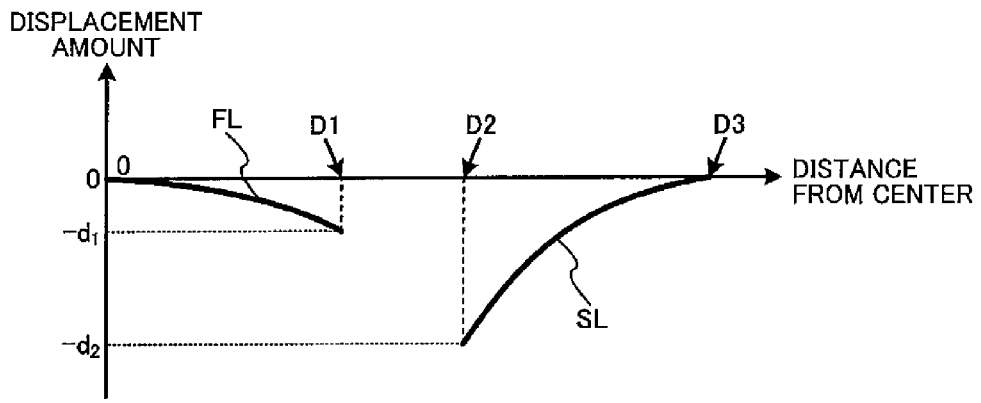

As illustrated in FIG. 8C, when the front-field-of-view image is demagnified, and the side-field-of-view image is magnified to correct the boundary region, the displacement amount due to the magnification/demagnification process is negative in the front-field-of-view image and the side-field-of-view image.

The relationship between the magnification/demagnification factor and the displacement amount in the above examples is represented by the following expressions. The following expression (1) represents an example of the magnification/demagnification factor $V_f(r)$ applied to the front-field-of-view image with respect to the distance r from the center.

$$V_f(r) = \alpha_f r^4 - \beta_f r^2 - \gamma_f \tag{1}$$

The following expression (2) represents the displacement amount $D_f(r)$ of the front-field-of-view image. The maximum displacement amount (i.e., the displacement amount at the distance D1) is $D_f(D1)$. Note that $\int_{0 \to r}$ indicates integration in the interval [0, r].

$$D_f(r) = \int_{0 \to r} V_f(x) \times dx \tag{2}$$

The following expression (3) represents an example of the magnification/demagnification factor $V_s(r)$ applied to the side-field-of-view image with respect to the distance r from the center.

$$V_s(r) = \alpha_s r^4 + \beta_s r^2 + \gamma_s \tag{3}$$

The following expression (4) represents the displacement amount $D_S(r)$ of the side-field-of-view image. The maximum displacement amount (i.e., the displacement amount at the distance D2) is $D_s(D2)$. Note that $\int_{D3 \to r}$ indicates integration in the interval [D3, r].

$$D_s(r) = \int_{D3 \to r} V_s(x) \times dx \tag{4}$$

The maximum displacement amount $D_f(D1)$ of the front-field-of-view image and the maximum displacement amount $D_s(D2)$ of the side-field-of-view image satisfy the relationship represented by the following expression (5).

$$D1 + D_f(D1) \geq D2 + D_s(D2) \tag{5}$$

For example, the entire or local display ratio of the front-field-of-view image to the side-field-of-view image may be arbitrarily changed while correcting the boundary region by changing the observation mode by operating the switch of the external I/F section 500, and changing the magnification/demagnification factor parameters $\alpha_f$, $\beta_f$, $\gamma_f$, $\alpha_s$, $\beta_s$, and $\gamma_s$. This makes it possible to arbitrarily magnify the observation target lesion area.

According to the first embodiment, it is possible to prevent a situation in which the boundary region between the front-field-of-view image and the side-field-of-view image is erroneously determined to be a shadow of folds, and arbitrarily change the display magnification of the front-field-of-view image and the side-field-of-view image. This contributes to an improvement in lesion area detection rate.

The coefficients $\alpha_f$, $\beta_f$, $\alpha_s$, and $\beta_s$ used to calculate the magnification/demagnification factor $V_f(r)$ or $V_s(r)$ may be 0. In this case, the magnification/demagnification process can be performed using a constant magnification/demagnification factor $\gamma_f$ or $\gamma_s$ independently of the distance r from the center.

Figure 9:
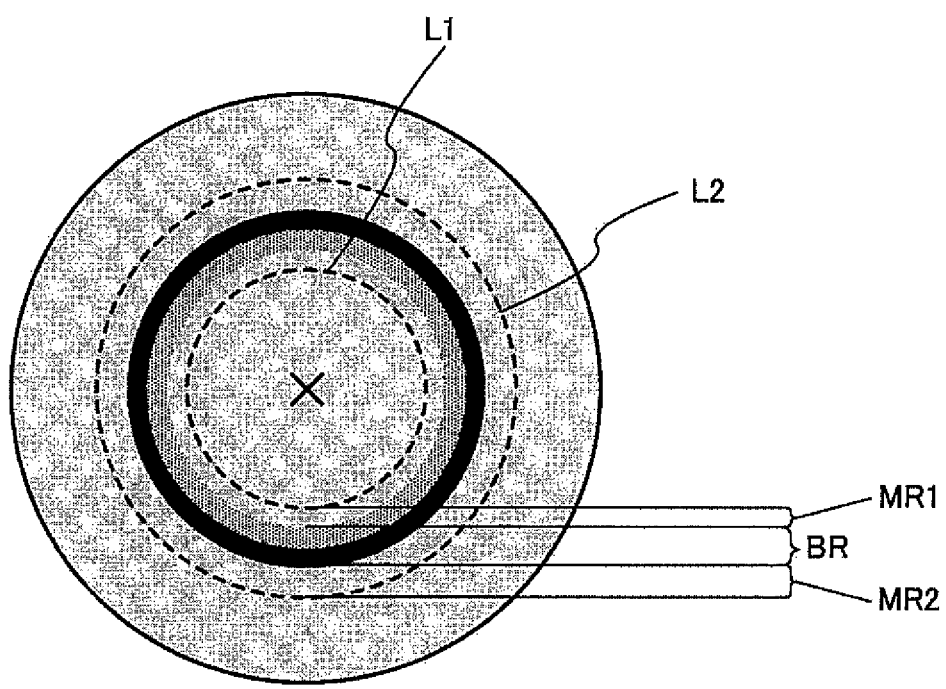
FIG. 9 is a view illustrating a modification of an extraction boundary line setting method.

As illustrated in FIG. 9, the extraction boundary lines L1 and L2 may be set while providing margin regions MR1 and MR2. MR1 is a margin region between the boundary region BR and the extraction boundary line L1, and MR2 is a margin region between the boundary region BR and the extraction boundary line L2. The boundary region BR is a region that is determined to be an angle of view that is inappropriate for observation based on the optical design, and sufficient margin regions MR1 and MR2 may be provided around the boundary region BR taking account of a statistical production variation. In this case, since it is unnecessary to provide the memory 211 that stores the extraction boundary lines L1 and L2 specific to each imaging section 200, the cost of the imaging section 200 can be reduced.

According to the first embodiment, an endoscope image processing device includes the image acquisition section 305 and the boundary region correction section 315 (see FIG. 5). As described above with reference to FIG. 4, the image acquisition section 305 acquires image signals that form a front image (front-field-of-view image 23) corresponding to the front field of view and a side image (side-field-of-view image 24) corresponding to the side field of view as a single acquired image. As described above with reference to FIGS. 6A to 7D, the boundary region correction section 315 performs an overlapping process that causes at least one of the image FR of a front region and the image SR of a side region to overlap the boundary region BR that is a region that defines the boundary between the front region and the side region, the front region being a region within the acquired image that corresponds to the front field of view, and the side region being a region within the acquired image that corresponds to the side field of view.

The above configuration makes it possible to suppress a deterioration in visibility due to the boundary region BR. Specifically, since shading in the boundary region BR can be eliminated by correcting the boundary region BR, it is possible to prevent a situation in which shading is erroneously determined to be a shadow of folds. Moreover, since a region unnecessary for diagnosis can be removed from the display image, it is possible to improve the lesion determination efficiency.

The term "overlapping process" used herein refers to a process that causes a different image to overlap a specific region (e.g., boundary region) of an image. For example, the overlapping process is implemented by overwriting data that indicates a different image (e.g., an image subjected to the magnification/demagnification process) in a memory area of an image memory that corresponds to a specific region of an image. Alternatively, the overlapping process is implemented by deleting a specific region from an image, and synthesizing the image and another image as a single image.

The term "boundary region" used herein refers to a shading region that is present between the front region and the side region. For example, the boundary region is a region that occurs due to a blind spot between the front observation optical system and the side observation optical system, or occurs due to limb darkening that occurs due to the front observation optical system. The front field of view and the side field of view may be captured in time series (see above). In this case, the boundary region is a shading region that has occurred in a single image obtained by synthesizing the front image and the side image due to the imaging optical system, the synthesis process, or the like.

In the first embodiment, the boundary region correction section 315 may include the magnification/demagnification section 325 and the synthesis section 350 (see FIG. 5). The magnification/demagnification section 325 may perform the magnification/demagnification process that changes the display magnification of at least one of the image FR of the front region and the image SR of the side region. The synthesis section 350 may perform the overlapping process by synthesizing the image of the front region and the image of the side region subjected to the magnification/demagnification process.

More specifically, the boundary region correction section 315 may include the region extraction section 320. As described above with reference to FIGS. 6A to 7E, the region extraction section 320 may extract one of the image FR of the front region and the image SR of the side region from the acquired image as the target image that is subjected to the magnification/demagnification process. The magnification/demagnification section 325 may perform the magnification/demagnification process that magnifies the target image. The synthesis section 350 may synthesize the magnified target region (FR' or SR') and the other (SR or FR) of the front region and the side region.

For example, the magnification/demagnification section 325 may perform the magnification/demagnification process that magnifies the target image along the radial direction relative to the center CP of the front-field-of-view image FR, as described above with reference to FIGS. 6A and 7B. The magnification process along the radial direction may be a process that magnifies the target image in the direction away from the center CP (see FIG. 6B), or may be a process that magnifies the target image in the direction toward the center CP (see FIG. 7B). The magnification process along the radial direction may be a process that magnifies the inner side of the target image in the direction toward the center CP, and magnifies the outer side of the target image in the direction away from the center CP.

According to the above configuration, the overlapping process within the boundary region BR can be performed by magnifying one of the image FR of the front region and the image SR of the side region, and synthesizing the magnified image with the other image. Since only one of the image FR of the front region and the image SR of the side region is subjected to the magnification/demagnification process, hardware (e.g., image memory) can be economized.

As described above with reference to FIGS. 8A to 8C, the magnification/demagnification section 325 may perform the magnification/demagnification process that magnifies one of the image FR of the front region and the image SR of the side region, and perform the magnification/demagnification process that demagnifies the other of the image FR of the front region and the image SR of the side region. The synthesis section 350 may synthesize the image of the front region and the image of the side region subjected to the magnification/demagnification process.

According to the above configuration, the overlapping process within the boundary region BR can be performed by magnifying one of the image FR of the front region and the image SR of the side region, demagnifying the other of the image FR of the front region and the image SR of the side region, and synthesizing the resulting images. Since the image FR of the front region and the image SR of the side region can be arbitrarily magnified or demagnified the observation area can be arbitrarily magnified. For example, the image FR of the front region can be magnified when observing a lesion area situated in the center area of the field of view, and the image SR of the side region can be magnified when observing the back of folds in the side area of the field of view side during screening.

In the first embodiment, the endoscope image processing device may include the boundary line drawing section 360 (see FIG. 5). As described above with reference to FIG. 6D and the like, the boundary line drawing section 360 may draw the boundary line WL that defines the boundary between the image of the front region and the image of the side region that have been synthesized.

The above configuration makes it possible to clearly display the boundary between the image of the front region and the image of the side region. Specifically, since a blind spot occurs due to the optical system (see FIG. 4A and the like), and the boundary region BR corresponding to the blind spot is covered by the overlapping process, the boundary between the image of the front region and the image of the side region is discontinuous in the synthesized image. For example, the user may be confused when a pair of forceps or the like is situated at the boundary. It is possible to reduce such a confusing situation by drawing the boundary line.

In the first embodiment, the boundary region may be the annular region 25 that corresponds to a specific angle of view based on the optical design value of the optical system (lens 20) for capturing the front field of view and the side field of view (see FIGS. 4A to 4C). As described above with reference to FIG. 9, the first boundary line L1 that is the boundary line between the boundary region BR and the front region may be set on the inner side relative to the annular region BR. The second boundary line L2 that is the boundary line between the boundary region BR and the side region may be set on the outer side relative to the annular region BR.

The above configuration makes it possible to extract the front region that is situated on the inner side relative to the boundary region BR and the side region that is situated on the outer side relative to the boundary region BR (i.e., extract a region that excludes the boundary region BR).

In the first embodiment, the first boundary line L1 and the second boundary line L2 may be set in a state in which the margin regions MR1 and MR2 are added to (provided around) the annular region BR that corresponds to a specific angle of view corresponding to a statistical production variation.

According to the above configuration, since it is unnecessary to set the boundary lines L1 and L2 corresponding to each scope taking account of a production variation, it is possible to use common boundary lines L1 and L2. This makes it unnecessary to perform the boundary line setting process corresponding to each scope, for example.

In the first embodiment, the endoscope system may include a front observation optical system (i.e., the transmission part 21 of the lens 20) for capturing the front field of view, and a side observation optical system (i.e., the reflective parts 22 and 26 of the lens 20) for capturing the side field of view (see FIG. 4A and the like). The endoscope system may include the image sensor 209 that simultaneously captures the front field of view and the side field of view (see FIG. 1).

The above configuration makes it possible to simultaneously capture the front field of view and the side field of view within a single image. Note that the optical system is not limited to the above optical system. For example, the front field of view and the side field of view may be captured in time series using an optical system in which an optical system for capturing the front field of view and an optical system for capturing the side field of view are not separately provided. In this case, images captured in time series may be synthesized to obtain a single image (see FIG. 5).

In the first embodiment, the boundary region may include a region that corresponds to a blind spot between the front field of view obtained through the front observation optical system and the side field of view obtained through the side observation optical system (see FIG. 4A and the like). The boundary region may include at least part of a region in which shading occurs due to limb darkening that occurs due to the front observation optical system. For example, the boundary region includes a limb darkening region that has a brightness lower than a given brightness in a state in which the gray patch is captured (see above).

3. Second Embodiment 3.1. Endoscope System

Figure 10:
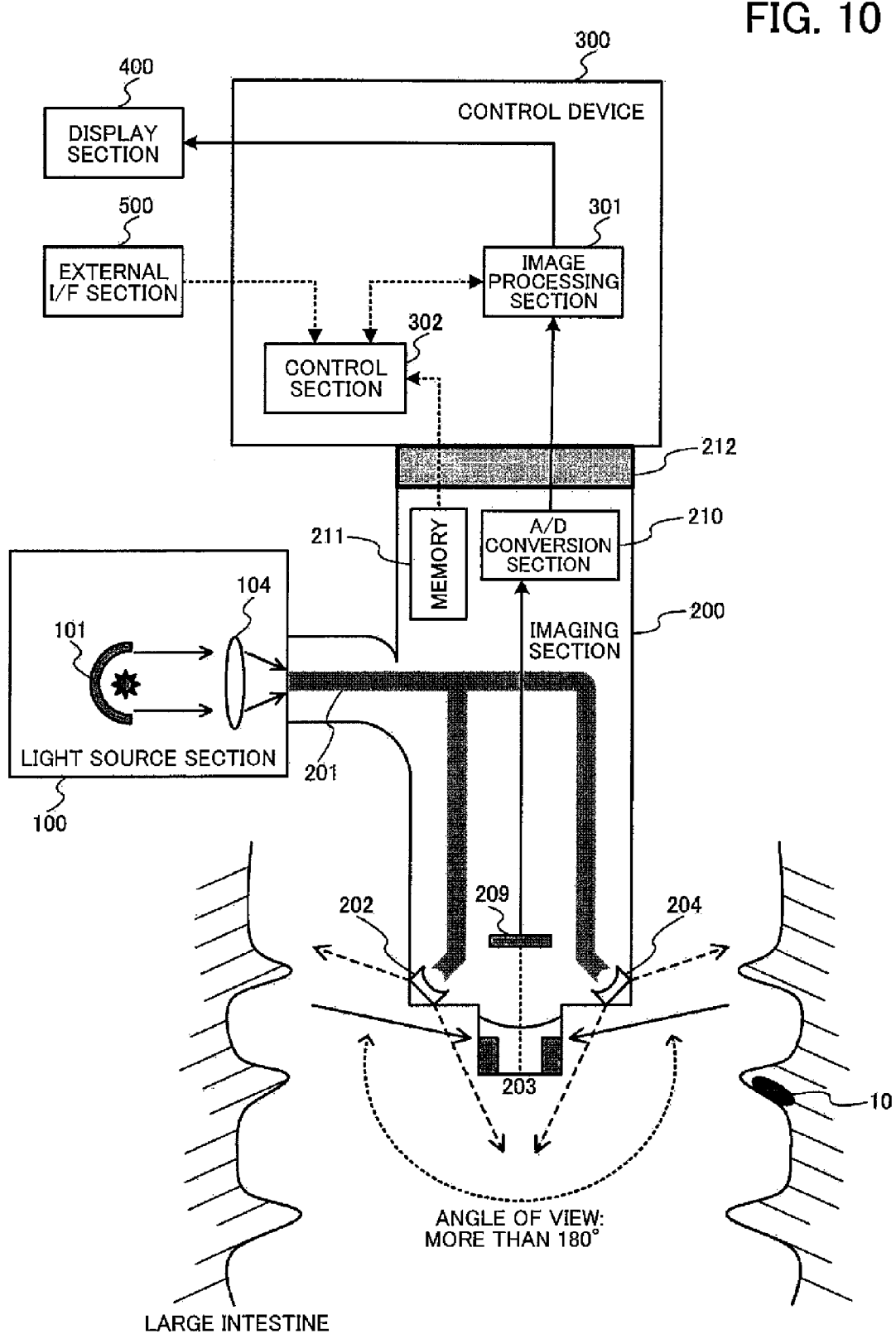
FIG. 10 illustrates a second configuration example of an endoscope system.

FIG. 10 illustrates a second configuration example of an endoscope system. The endoscope system includes a light source section 100, an imaging section 200, a control device 300 (processor section), a display section 400, and an external I/F section 500. The following description mainly focuses on the elements that differ from those described above in connection with the first configuration example, and description of the same elements as those described above in connection with the first configuration example is appropriately omitted.

The light source section 100 includes a white light source 101, and a condenser lens 104 that focuses light emitted from the white light source 101 on the incident end face of a light guide fiber 201. In the second configuration example, a rotary color filter is not provided.

In the second configuration example, a primary-color single-chip image sensor is used as the image sensor 209 included in the imaging section 200. The primary-color single-chip image sensor is an image sensor having a Bayer array. A CCD image sensor or a CMOS image sensor may be used as the primary-color single-chip image sensor.

3.2. Image Processing Section

Figure 12:
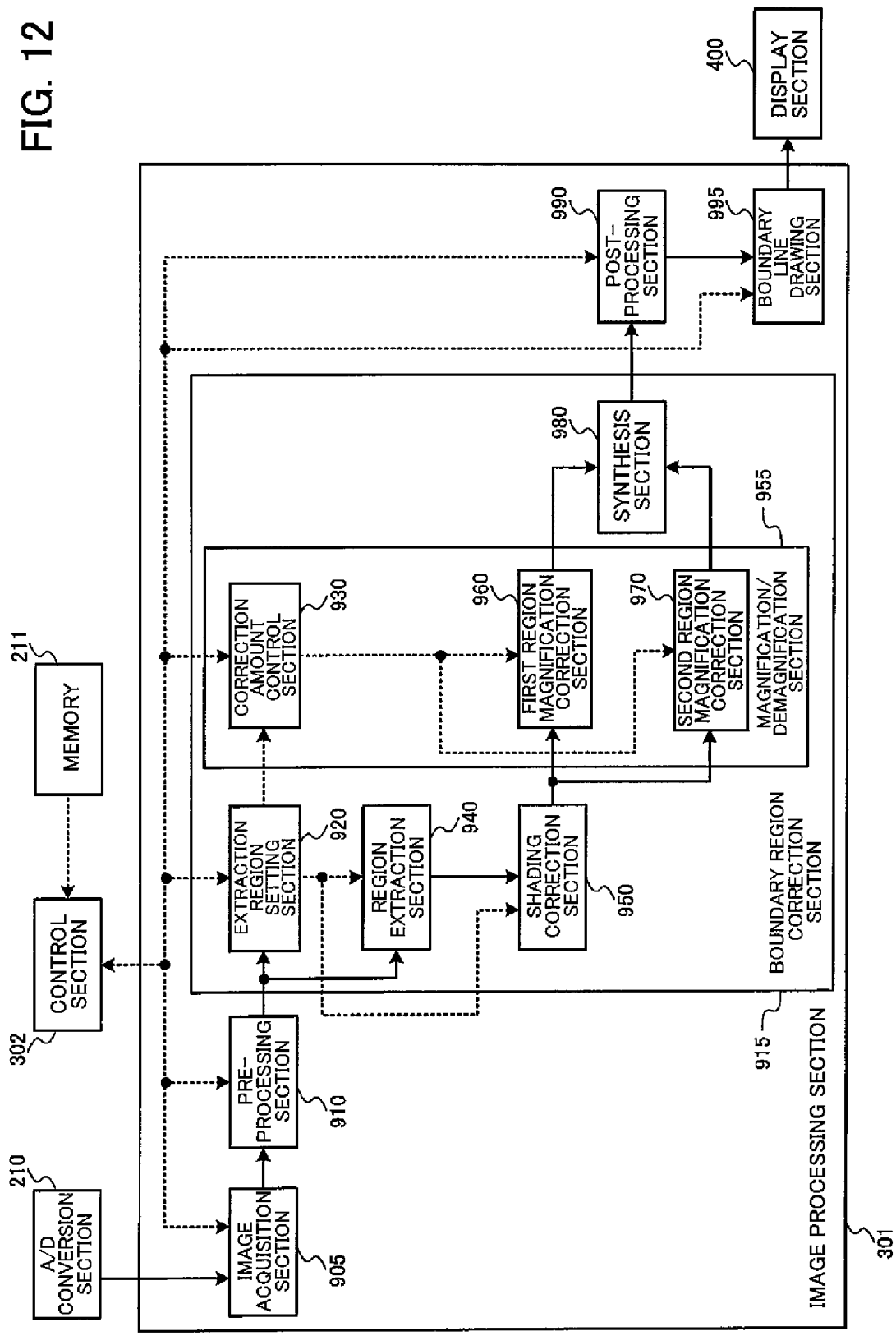
FIG. 12 illustrates a second detailed configuration example of an image processing section.

FIG. 12 illustrates a second detailed configuration example of the image processing section 301. The image processing section 301 includes an image acquisition section 905, a preprocessing section 910, a boundary region correction section 915, a post-processing section 990, and a boundary line drawing section 995. The boundary region correction section 915 includes an extraction region setting section 920, a region extraction section 940, a shading correction section 950, a magnification/demagnification section 955, and a synthesis section 980. The magnification/demagnification section 955 includes a correction amount control section 930, a first region magnification correction section 960, and a second region magnification correction section 970.

The connection relationship and the flow of data between each section are described below. The captured image output from the A/D conversion section 210 is input to the image acquisition section 905. The image acquired by the image acquisition section 905 is input to the preprocessing section 910. The control section 302 is bidirectionally connected to the image acquisition section 905, the preprocessing section 910, the extraction region setting section 920, the correction amount control section 930, the post-processing section 990, and the boundary line drawing section 995. The control section 302 reads the information specific to the imaging section 200 (e.g., the extraction boundary information about the front-field-of-view image and the side-field-of-view image, and the display magnification information about the front-field-of-view image and the side-field-of-view image) that is stored in the memory 211, and updates the information stored in the memory 211.

The preprocessing section 910 corrects the input captured image based on the output image generation parameter (OB clamp and white balance) output from the control section 302, and outputs the corrected captured image to the extraction region setting section 920 and the region extraction section 940.

The extraction region setting section 920 performs an extraction region setting process when an extraction region setting signal output from the control section 302 is set to ON, and outputs extraction region information to the correction amount control section 930, the control section 302, and the region extraction section 940. The extraction region setting section 920 also outputs a shading correction coefficient to the shading correction section 950. The term "extraction region information" used herein refers to information about the center position of the front-field-of-view image and the side-field-of-view image, information about the front-field-of-view image extraction boundary line, information about the side-field-of-view image extraction boundary line, and information about the outer edge of the side-field-of-view image (see the first embodiment). For example, the extraction region information includes information about the coordinates of the center position CP (see FIG. 6A, for example), and the distances D1, D2, and D3 from the center position CP (see FIG. 8A, for example) in the polar coordinate system having the center position CP as the origin. The details of the extraction region setting process are described later.

The extraction region setting signal is ON/OFF-controlled using the switch of the external I/F section 500. For example, the extraction region setting signal is set to ON when the user has selected a white balance coefficient calculation mode by operating the switch of the external I/F section 500. The extraction region setting signal is set to OFF during normal examination.

The correction amount control section 930 performs a correction amount control process based on an observation mode switch signal output from the control section 302. The correction amount control section 930 sets magnification correction information about the front-field-of-view image and magnification correction information about the side-field-of-view image based on the extraction region information input from the extraction region setting section 920, outputs the magnification correction information about the front-field-of-view image to the first region magnification correction section 960, and outputs the magnification correction information about the side-field-of-view image to the second region magnification correction section 970. For example, the magnification correction information is given using the coefficients of the polynomial expressions (1) and (3) (see the first embodiment).

The captured image subjected to the white balance process that has been output from the preprocessing section 910 is input to the region extraction section 940. The region extraction section 940 extracts the front-field-of-view image and the side-field-of-view image from the input captured image based on the extraction region information output from the extraction region setting section 920, and outputs the extracted front-field-of-view image and the extracted side-field-of-view image to the shading correction section 950.

The shading correction section 950 performs a shading correction process on the front-field-of-view image and the side-field-of-view image input from the region extraction section 940 using the shading correction coefficient output from the extraction region setting section 920. The shading correction section 950 outputs the corrected front-field-of-view image to the first region magnification correction section 960, and outputs the corrected side-field-of-view image to the second region magnification correction section 970.

Figure 11:
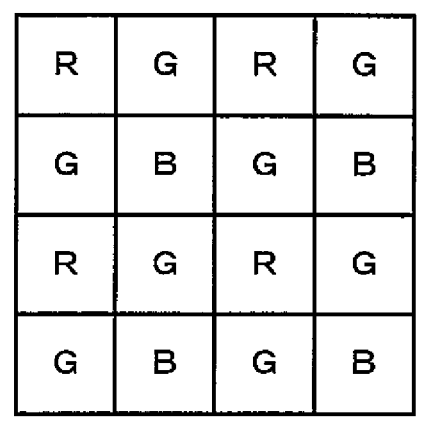

The first region magnification correction section 960, the second region magnification correction section 970, and the synthesis section 980 basically operate in the same manner as in the first embodiment, provided that each pixel of the captured image consists of three color signals in the first embodiment, while each pixel of the captured image consists of one color signal in the second embodiment. In the second embodiment, the magnification correction process is performed so that the signal array illustrated in FIG. 11 is maintained after the magnification correction process has been performed on the front-field-of-view image and the side-field-of-view image. Specifically, an interpolation process is performed using peripheral pixels in the same color to generate a single color signal at a given pixel position.

The captured image output from the synthesis section 980 in which the front-field-of-view image and the side-field-of-view image are synthesized is input to the post-processing section 990. The post-processing section 990 performs a demosaicing process, a color correction process, a grayscale transformation process, an enhancement process, a magnification process, and the like on the input captured image to generate an output image that can be displayed on a display monitor, and outputs the output image to the boundary line drawing section 995.

The process performed by the boundary line drawing section 995 is the same as described above in connection with the first embodiment, and description thereof is omitted.

3.3. Extraction Region Setting Section

Figure 13:
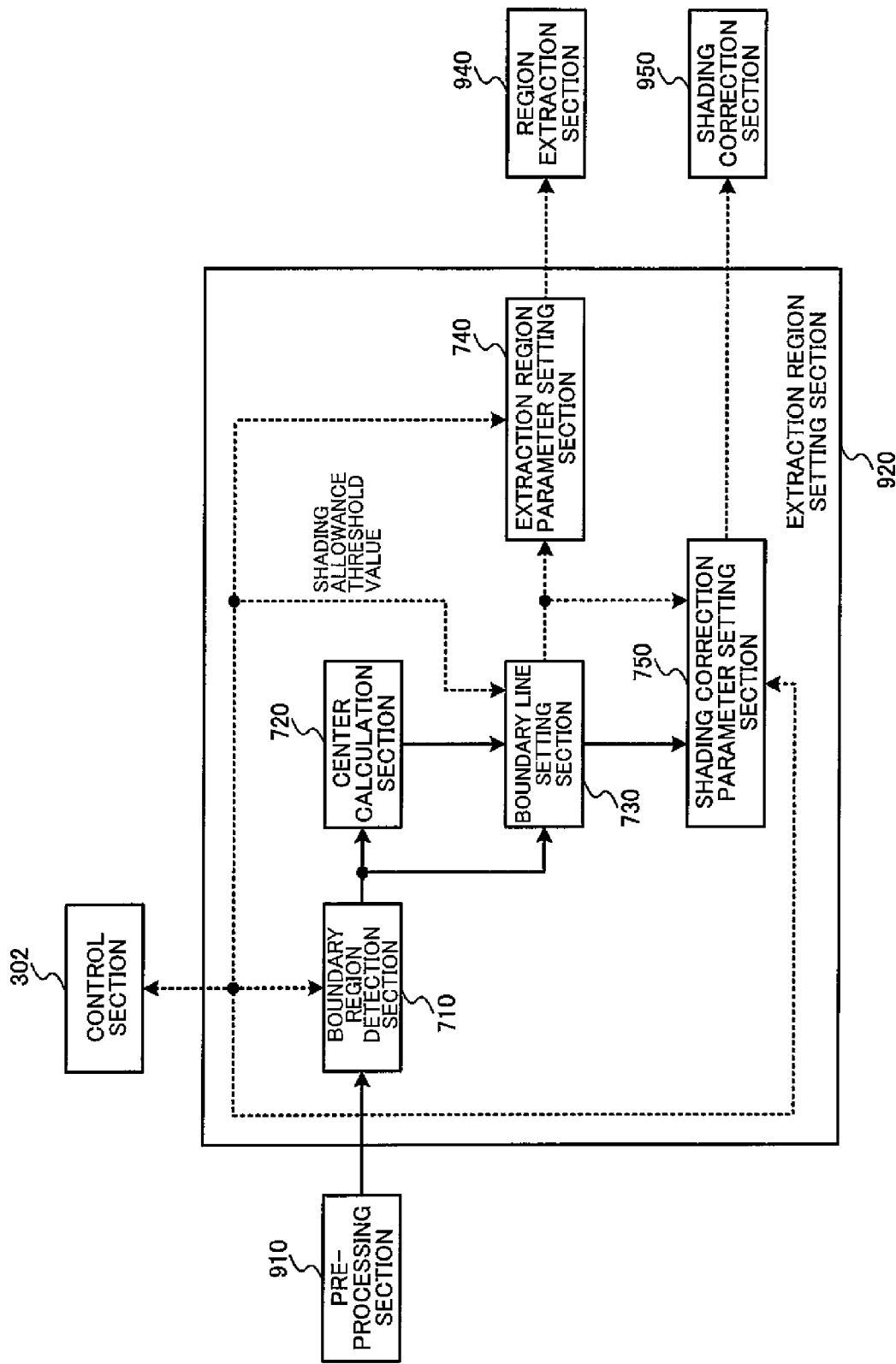
FIG. 13 illustrates a detailed configuration example of an extraction region setting section.

FIG. 13 illustrates a detailed configuration example of the extraction region setting section 920. The extraction region setting section 920 includes a boundary region detection section 710, a center calculation section 720, a boundary line setting section 730 (extraction boundary line determination section), an extraction region parameter setting section 740, and a shading correction parameter setting section 750.

The connection relationship and the flow of data between each section are described below. The captured image output from the preprocessing section 910 is input to the boundary region detection section 710. Note that the object within the captured image is a white patch for calculating the white balance coefficient, and an image can be captured in a state in which the relative positional relationship between the end of the imaging section 200 and the white patch is maintained.

The control section 302 is bidirectionally connected to the boundary region detection section 710, the boundary line setting section 730, the extraction region parameter setting section 740, and the shading correction parameter setting section 750.

The captured image subjected to the white balance process that is output from the preprocessing section 910 is input to the boundary region detection section 710. When the extraction region setting signal output from the control section 302 is set to ON, detection region information and a detection threshold value for detecting the boundary region are input from the control section 302. The boundary region detection section 710 extracts a detection region from the input captured image based on the detection region information, and sums the pixel values of adjacent 2×2 pixels (R, G, G, B) of the Bayer array illustrated in FIG. 11 to generate a brightness signal. The boundary region detection section 710 performs a binarization process through comparison between the generated brightness signal and a detection threshold value, and removes unnecessary thin lines from the brightness signal subjected to the binarization process to extract the boundary line. The boundary region detection section 710 outputs boundary line information about the extracted boundary line to the center calculation section 720, and outputs the generated brightness signal to the boundary line setting section 730.

The center calculation section 720 calculates the center-of-gravity position from the input boundary line information, sets the center-of-gravity position to be the center position of the front-field-of-view image and the side-field-of-view image, and outputs the center position to the boundary line setting section 730.

The boundary line setting section 730 determines a shading allowance position of the input brightness signal based on a shading allowance threshold value output from the control section 302. Specifically, the boundary line setting section 730 calculates a shading image by dividing the brightness value within the detection region (e.g., the entire image) by the average brightness value around the center position CP (i.e., shading reference value) (see FIG. 14A). The boundary line setting section 730 determines the shading allowance position from the calculated shading image and the shading allowance threshold value (T) input from the control section 302, and determines the annular extraction boundary lines L1 and L2 that are situated closest to the center position. The boundary line setting section 730 outputs the determined extraction boundary lines L1 and L2 to the extraction region parameter setting section 740 and the shading correction parameter setting section 750, and outputs the calculated shading image to the shading correction parameter setting section 750.

Figure 14B:
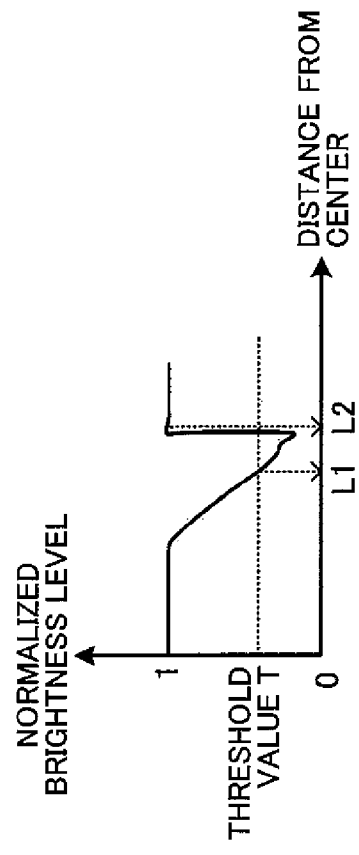
FIGS. 14A to 14C are views illustrating a shading correction process.

More specifically, the boundary line setting section 730 calculates a position at which the brightness level of the shading image is equal to a threshold value T, and calculates the distance from the center to the calculated position (see FIG. 14B). The boundary line setting section 730 sets a circle having a radius that is equal to one of the calculated distances, whichever is shorter, to be the extraction boundary line L1. The boundary line setting section 730 sets a circle having a radius that is calculated by adding a given distance to the other of the calculated distances to be the extraction boundary line L2.

The extraction region parameter setting section 740 sets information about the radius and the center coordinates of the extraction boundary lines L1 and L2 to be the extraction region parameters, and stores the extraction region parameters in the memory 211 through the control section 302. The extraction region parameter setting section 740 outputs the extraction region parameters to the region extraction section 940.

Figure 14C:
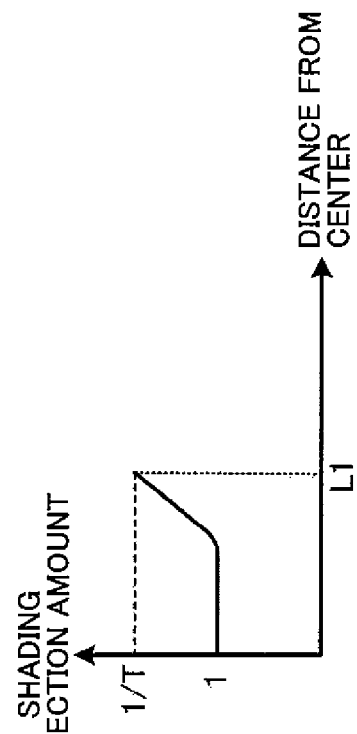
Figure 14A:
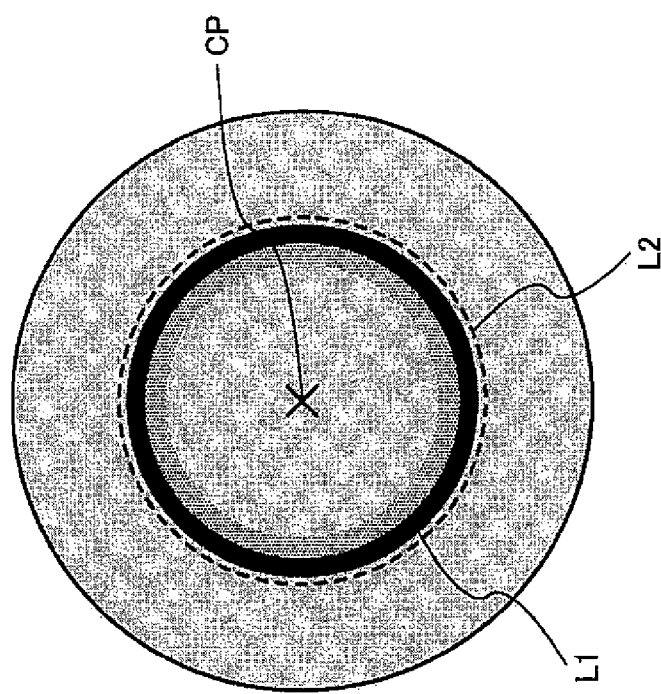

The shading correction parameter setting section 750 calculates a shading correction coefficient image or the shading correction coefficient from the input extraction boundary lines L1 and L2, the center position, and the shading image. The shading correction parameter setting section 750 sets the shading correction coefficient image or the shading correction coefficient to be a shading correction parameter, and stores the shading correction parameter in the memory 211 through the control section 302. The shading correction parameter setting section 750 outputs the shading correction parameter to the shading correction section. Note that the shading correction coefficient image is an image generated by calculating a reciprocal of each pixel value of the shading image relative to the center position. The shading correction coefficient (shading correction amount) is a coefficient (one-dimensional coefficient in the radial direction) that is calculated by averaging the pixel values of the shading correction coefficient image in the circumferential direction (see FIG. 14C).

The extraction region setting section 920 outputs the parameter stored in the memory 211 to the extraction region parameter setting section 740 and the shading correction parameter setting section 750 when the extraction region setting signal output from the control section 302 is set to OFF, and outputs the resulting parameter to the region extraction section 940 and the shading correction section 950.

Although an example in which the shading correction process is performed on only the front-field-of-view image has been described above, another configuration may also be employed. For example, the shading correction process may be performed on the front-field-of-view image and the side-field-of-view image.

According to the second embodiment, the boundary region correction section 915 includes the boundary line setting section 730 and the region extraction section 940 (see FIGS. 12 and 13). The boundary line setting section 730 sets at least one of the first boundary line L1 (i.e., the boundary line for extracting the image of the front region from the acquired image) and the second boundary line L2 (i.e., the boundary line for extracting the image of the side region from the acquired image) (see FIG. 14A). The region extraction section 940 extracts the image of the front region based on the first boundary line L1 when the first boundary line L1 has been set by the boundary line setting section 730. The region extraction section 940 extracts the image of the side region based on the second boundary line L2 when the second boundary line L2 has been set by the boundary line setting section 730.

More specifically, the boundary region correction section 915 may include the boundary region detection section 710 that detects the boundary region (see FIG. 13). As described above with reference to FIG. 14B, the boundary line setting section 730 may set at least one of the first boundary line L1 and the second boundary line L2 based on the detected boundary region.

The above configuration makes it possible to set at least one of the first boundary line L1 and the second boundary line L2, and set at least one of the front region and the side region using the boundary line. Although an example in which both the image of the front region and the image of the side region are extracted has been described above, one of the image of the front region and the image of the side region may be extracted, and the shading correction process and the overlapping process may then be performed.

In the second embodiment, the boundary line setting section 730 may set the first boundary line L1 based on the shading amount that indicates a change in brightness level in the acquired image (e.g., a brightness value that is normalized using the average brightness value around the center of the acquired image) (see FIG. 14B). The region extraction section 940 may extract an image of the region of the acquired image that is situated on the inner side relative to the first boundary line L1 as the image of the front region.

More specifically, the boundary region correction section 915 may include the shading correction section 950 that corrects the shading amount in the front region (see FIG. 12). The synthesis section 980 may synthesize the image of the front region for which the shading amount has been corrected, with the image of the side region.

According to the above configuration, a shading region in the image that has occurred due to the optical system (e.g., limb darkening in the front region) can be displayed at a brightness similar to that of a non-shading region. Therefore, a region in which shading has occurred can also be used as the display image, and occurrence of a blind-spot region (i.e., a region that cannot be observed) can be minimized. Moreover, since the extraction boundary lines L1 and L2 can be determined under specific imaging conditions (e.g., during white balance cap imaging), a reduction in the number of adjustment steps required due to a production variation, and a reduction in cost can be achieved.

In the second embodiment, the magnification/demagnification section 955 may include a display magnification setting section (correction amount control section 930) (see FIG. 12). The first boundary line L1 and the second boundary line L2 may be circular boundary lines. The display magnification setting section may set the display magnification relative to the center point CP of the first boundary line L1 and the second boundary line L2 (e.g., the magnification/demagnification factors $V_f(r)$ and $V_s(r)$ (see the expressions (1) and (3)). The magnification/demagnification section 955 may perform the magnification/demagnification process based on the display magnification set by the display magnification setting section.

More specifically, the magnification/demagnification section 955 may perform the magnification/demagnification process using a displacement amount that is based on the display magnification set by the display magnification setting section, and is linear or nonlinear relative to the distance (r) from the center point CP in the radial direction (e.g., the displacement amounts $D_f(r)$ and $D_s(r)$ (see the expressions (2) and (4))).

The above configuration makes it possible to magnify or demagnify the front region and the side region using an arbitrary magnification/demagnification factor. Moreover, since linear or nonlinear magnification/demagnification relative to the distance from the center can be performed, it is possible to implement a magnification/demagnification process with a higher degree of freedom corresponding to the observation area.

Although the above embodiments have been described taking an example in which the boundary lines L1 and L2 form a true circle, the configuration is not limited thereto. It suffices that the boundary lines L1 and L2 be circular. Specifically, it suffices that the boundary region be present between the boundary lines L1 and L2.

The embodiments according to the invention and the modifications thereof have been described above. Note that the invention is not limited to the above embodiments and the modifications thereof. Various modifications and variations may be made without departing from the scope of the invention. A plurality of elements described in connection with the above embodiments and the modifications thereof may be appropriately combined to implement various configurations. For example, some of the elements described in connection with the above embodiments and the modifications thereof may be omitted. Some of the elements described above in connection with different embodiments or modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

What is claimed is:

1. An endoscope image processing device comprising:
   an image acquisition section that acquires image signals that form a front image corresponding to a front field of view and a side image corresponding to a side field of view as a single acquired image; and
   a boundary region correction section that performs an overlapping process that causes at least one of an image of a front region and an image of a side region to overlap a boundary region that is a region that defines a boundary between the front region and the side region, the front region being a region within the acquired image that corresponds to the front field of view, and the side region being a region within the acquired image that corresponds to the side field of view,
   wherein the boundary region is an annular region that corresponds to a specific angle of view based on an optical design value of an optical system for capturing the front field of view and the side field of view, and
   wherein the boundary region correction section includes a boundary line setting section that sets a first boundary line that is a boundary line between the boundary region and the front region and that is set on an inner side relative to the annular region that corresponds to the specific angle of view, and a second boundary line that is a boundary line between the boundary region and the side region and that is set on an outer side relative to the annular region that corresponds to the specific angle of view.

2. The endoscope image processing device as defined in claim 1, wherein the boundary region correction section further includes:
   a magnification/demagnification section that performs a magnification/demagnification process that changes a display magnification of at least one of the image of the front region and the image of the side region; and
   a synthesis section that performs the overlapping process by synthesizing the image of the front region and the image of the side region subjected to the magnification/demagnification process.

3. The endoscope image processing device as defined in claim 2, wherein:
   the boundary region correction section further includes a region extraction section that extracts one of the image of the front region and the image of the side region from the acquired image as a target image that is subjected to the magnification/demagnification process, the magnification/demagnification section performs the magnification/demagnification process that magnifies the target image, and the synthesis section synthesizes the magnified target image and the other of the image of the front region and the image of the side region.

4. The endoscope image processing device as defined in claim 3, wherein the magnification/demagnification section performs the magnification/demagnification process that magnifies the target image along a radial direction relative to a center of the front image.

5. The endoscope image processing device as defined in claim 2, wherein:

the boundary region correction section further includes a region extraction section that extracts the image of the front region and the image of the side region from the acquired image, the magnification/demagnification section performs the magnification/demagnification process that magnifies one of the image of the front region and the image of the side region, and performs the magnification/demagnification process that demagnifies the other of the image of the front region and the image of the side region, and the synthesis section synthesizes the image of the front region and the image of the side region subjected to the magnification/demagnification process.

6. The endoscope image processing device as defined in claim 2, wherein the boundary line setting section that sets at least one of the first boundary line and the second boundary line, the first boundary line being a boundary line for extracting the image of the front region from the acquired image, and the second boundary line being a boundary line for extracting the image of the side region from the acquired image; and wherein the boundary region correction section further includes a region extraction section that extracts the image of the front region based on the first boundary line when the first boundary line has been set by the boundary line setting section, and extracts the image of the side region based on the second boundary line when the second boundary line has been set by the boundary line setting section.

7. The endoscope image processing device as defined in claim 6, wherein:

the boundary region correction section further includes a boundary region detection section that detects the boundary region, and the boundary line setting section sets said at least one of the first boundary line and the second boundary line based on the detected boundary region.

8. The endoscope image processing device as defined in claim 6, wherein:

the boundary line setting section sets the first boundary line based on a shading amount that indicates a change in brightness level in the acquired image, and the region extraction section extracts an image of a region of the acquired image that is situated on an inner side relative to the first boundary line as the image of the front region.

9. The endoscope image processing device as defined in claim 8, wherein:

the boundary region correction section includes a shading correction section that corrects the shading amount in the front region, and the synthesis section synthesizes the image of the front region for which the shading amount has been corrected, with the image of the side region.

10. The endoscope image processing device as defined in claim 6, wherein:

the first boundary line and the second boundary line are circular boundary lines, the magnification/demagnification section includes a display magnification setting section that sets the display magnification relative to a center point of the first boundary line and the second boundary line, and the magnification/demagnification section performs the magnification/demagnification process based on the display magnification set by the display magnification setting section.

11. The endoscope image processing device as defined in claim 10, wherein the magnification/demagnification section performs the magnification/demagnification process using a displacement amount that is based on the display magnification set by the display magnification setting section, and is linear or nonlinear relative to a distance from the center point in a radial direction.

12. The endoscope image processing device as defined in claim 2, further comprising a boundary line drawing section that draws a boundary line that defines a boundary between the image of the front region and the image of the side region that have been synthesized.

13. The endoscope image processing device as defined in claim 1, wherein the first boundary line and the second boundary line are set in a state in which margin regions are added to the annular region that corresponds to the specific angle of view corresponding to a statistical production variation.

14. An endoscope system comprising:

the endoscope image processing device as defined in claim 1;

a front observation optical system for capturing the front field of view;

a side observation optical system for capturing the side field of view; and an image sensor that simultaneously captures the front field of view and the side field of view.

15. The endoscope system as defined in claim 14, wherein the boundary region includes a region that corresponds to a blind spot between the front field of view obtained through the front observation optical system and the side field of view obtained through the side observation optical system.

16. The endoscope system as defined in claim 14, wherein the boundary region includes at least a part of a region in which shading occurs due to limb darkening that occurs due to the front observation optical system.

17. An image processing method comprising:

acquiring image signals that form a front image corresponding to a front field of view and a side image corresponding to a side field of view as a single acquired image;

setting an annular region that corresponds to a specific angle of view based on an optical design value of an optical system for capturing the front field of view and the side field of view to be a boundary region, setting a first boundary line that is a boundary line between the boundary region and a front region on an inner side relative to the annular region that corresponds to the specific angle of view, and setting a second boundary line that is a boundary line between the boundary region and a side region on an outer side relative to the annular region that corresponds to the specific angle of view, wherein the boundary region is a region that defines a boundary between the front region and the side region, the front region being a region within the acquired image that corresponds to the front field of view, and the side region being a region within the acquired image that corresponds to the side field of view; and performing an overlapping process that causes at least one of an image of the front region and an image of the side region to overlap the boundary region.

* * * * *